United States Patent [19]
Ishizawa

[11] Patent Number: 5,478,237
[45] Date of Patent: Dec. 26, 1995

[54] IMPLANT AND METHOD OF MAKING THE SAME

[75] Inventor: Hitoshi Ishizawa, Kawasaki, Japan

[73] Assignee: Nikon Corporation, Tokyo, Japan

[21] Appl. No.: 82,515

[22] Filed: Jun. 25, 1993

Related U.S. Application Data

[63] Continuation-in-part of Ser. No. 12,510, Feb. 2, 1993, abandoned.

[30] Foreign Application Priority Data

Feb. 14, 1992 [JP] Japan .................................. 4-028525

[51] Int. Cl.$^6$ ................................................ A61C 8/00
[52] U.S. Cl. ....................... 433/201.1; 433/173; 433/174; 623/16; 205/318; 204/181.5
[58] Field of Search ..................... 433/173, 174, 433/175, 176, 201.1; 623/901, 11, 16; 204/180.2, 181.5; 205/208, 318; 252/62.2; 427/2

[56] References Cited

U.S. PATENT DOCUMENTS

| | | | |
|---|---|---|---|
| 3,969,195 | 7/1976 | Dotzer et al. | 205/208 |
| 4,846,837 | 7/1989 | Kurze et al. | 623/66 |
| 5,185,075 | 2/1993 | Rosenberg et al. | 205/234 |
| 5,205,921 | 4/1993 | Shirkanzadeh | 205/318 |

FOREIGN PATENT DOCUMENTS

| | | | |
|---|---|---|---|
| 0219220 | 2/1985 | Germany | 205/208 |
| 1193656 | 8/1986 | Japan | 433/172 |

OTHER PUBLICATIONS

Ishizawa et al, "Formation and Evaluation of Titanium Anodic Oxide Film Containing Ca and P," *Bioceramics*, vol. 5, Proceedings of the 5th International Symposium on Ceramics in Medicine, Nov. 1992.

Buser et al., "Influence of Surface Characteristics on Bone Integration of Titanium Implants. A Histomorphometric Study in Miniature Pigs," Journal of Biomedical Materials Research, vol. 25, 889–902 (1991).

*Primary Examiner*—Cary E. O'Connor
*Attorney, Agent, or Firm*—Shapiro and Shapiro

[57] ABSTRACT

An implant comprises and implant base body, at least a surface of which is composed of titanium or titanium alloy, and an anodic oxidation film formed on the surface, the film containing Ca and P. The implant may further comprise a calcium phosphate compound such as hydroxyapatite precipitated on the anodic oxidation film. The implant may be prepared by subjecting the base body to anodic oxidation in an electrolyte containing Ca compound and P compound, thereby forming an anodic oxidation film containing Ca and P. In addition, the film may be subjected to a hydrothermal treatment, thereby forming a film of a calcium phosphate compound such as hydroxyapatite on the anodic oxide film.

7 Claims, 2 Drawing Sheets

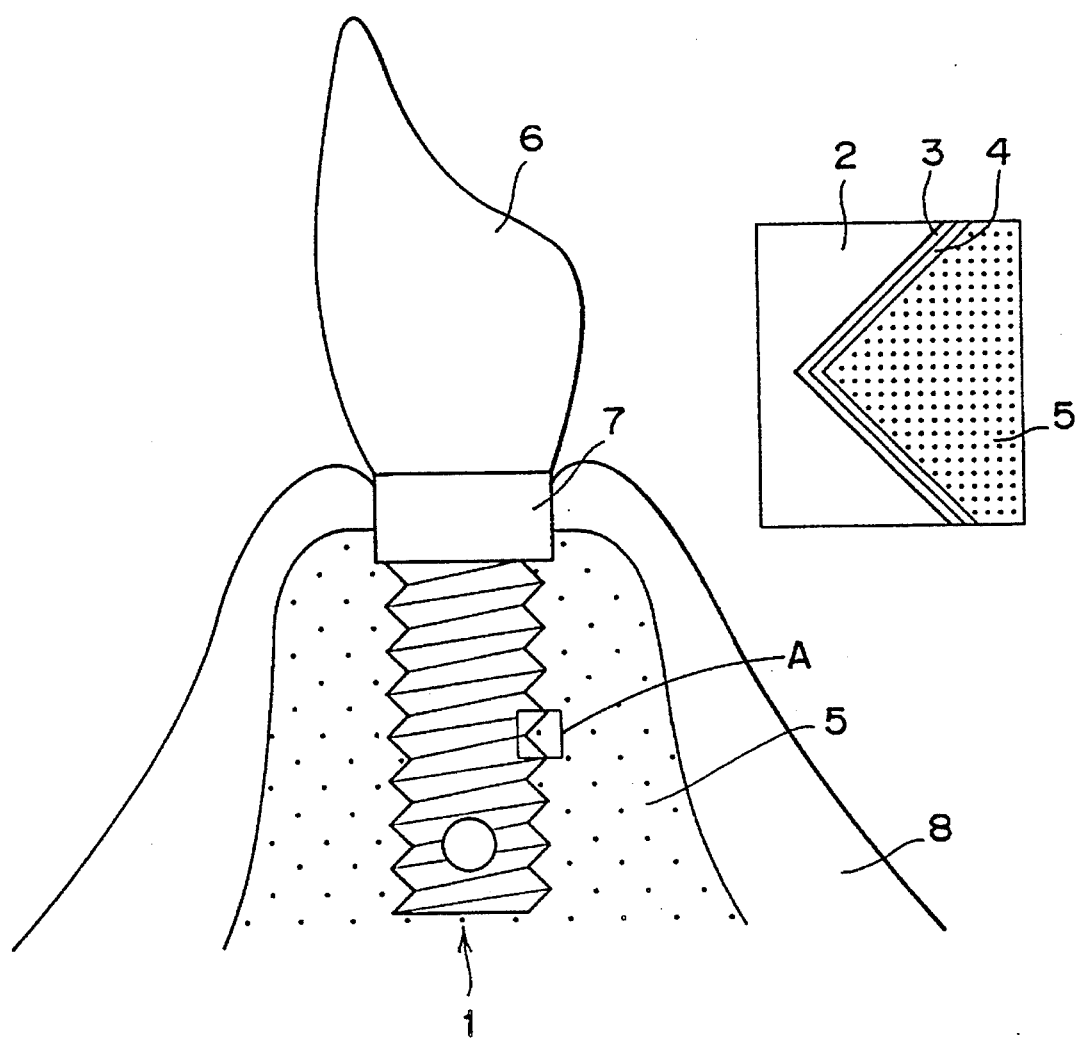

FIG. 3
FIG. 4
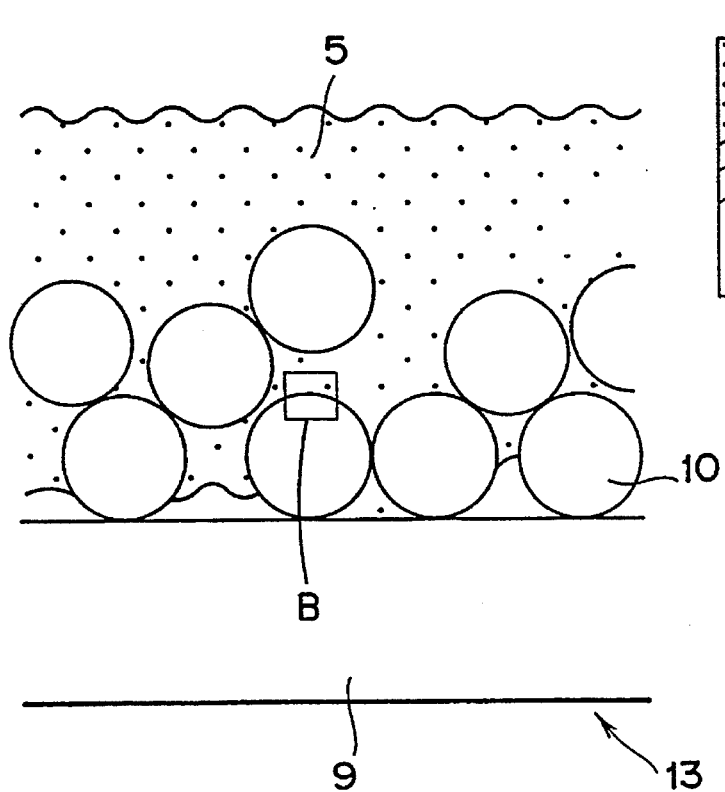
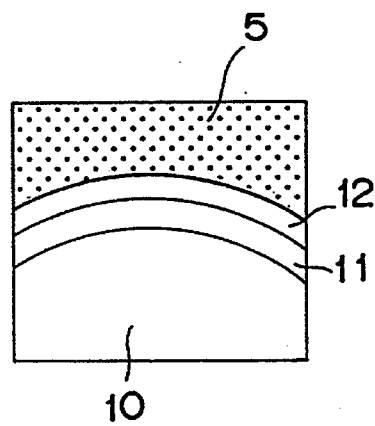

IMPLANT AND METHOD OF MAKING THE SAME

This is a continuation-in-part of application Ser. No. 012,510, filed Feb. 2, 1993 (abandoned).

BACKGROUND OF THE INVENTION

1. Field of the Invention

The present invention relates to dental and orthopedic implants including, for example, artificial tooth, artificial dental root, artificial bone, artificial articular, bone filler, bone screw, bond plate and bone frame. The present invention relates also to a method of making such implants.

More particularly, the present invention relates to an improved implant which is excellent in the affinity to bone tissue, and a method making of the same. The improved implant comprises a core and an anodic oxidation film formed on the core. The anodic oxidation film contains P and Ca in order to improve the affinity to the bone tissue in which the implant is implanted.

2. Related Background Art

In recent years, a remarkable progress has been made in medical techniques. With the arrival of "graying society", people are expecting a further and rapid development of this technical art. One developing technical field relates to new materials for bone substitute and bone reinforcement such as artificial dental root, artificial bone and artificial articular. They are now being accepted in the medical art more widely and rapidly. These new materials are generally called "implant" or "implant material". Mostly, they are made from metal, ceramics and other similar material.

Examples of the metallic material used for those implants which have already been put to practical use include stainless steel, Ni-Cr alloy, Co-Cr alloy, titanium and alloy thereof, and noble metal and alloy thereof. The selection of the most suitable material depends on the application of the final implant. Among others, at present, titanium and alloy thereof are preferably used since they have favorable properties such as high corrosion resistance, good bio-compatibility and excellent mechanical characteristics.

For those implants to be used, in particular, as artificial dental root and artificial bone, it is desirable that after implantation, the implant should be surrounded by the bone tissue as much as possible so as to keep the implant effective for a long time and stable in the living body. In order to attain this object, many methods have been proposed. One of the potential methods is to improve the affinity between implant and bone tissue by additionally treating the surface of the implant. According to a method proposed for this purpose, the surface of a titanium base body is coated with a layer of a biologically active (or compatible) material such as hydroxyapatite or other calcium phosphate compound by using the known plasma-spray technique thereby enabling a direct bonding between the implant surface and the bone tissue. Another method is to form a rough surface on the implant by plasma-spraying titanium powder. In a similar method, a porous surface layer is formed on the implant by sintering on it a large number of beads made of titanium or titanium alloy. These methods aim at increasing the mechanical engagement between implant and bone tissue so as to obtain a sufficient retention for the implant. However, it has been found that, as a practice matter, satisfactory implant cannot be prepared by using the techniques now available in the art as described above.

Besides the above methods, there are now being developed various means for obtaining the sufficient retention of the implant not only through the chemical bonding strength but also through some mechanical engagement between an implant and bone. For example, it has been proposed to form a large number of pores on the implant base plate by machining or cutting on it a thread. It has also been attempted to provide the implant with a rough surface by a chemical treatment, for example, etching with acid. There is also an attempt to additionally provide the rough surface with a coating of a biologically active material. In this case, it is essential for the coating to be stable in the living body and not to be exfoliated by the attack of biological cells or by degradation.

In the present standard of technique, however, it is very difficult to uniformly and firmly coat an implant having any complicated shape with biologically active material.

For example, by the plasma-spray technique, it is relatively easy to coat the outer surface of an implant with biologically active material. However, the coating of the inner surfaces of small through-holes and cylindrical ring portions is very difficult because the powder can hardly reach there. Similarly, in the case of those porous implants which have titanium beads or titanium alloy beads sintered on the implants and also those porous titanium implants to be used for filling the lost portion of a bone, it is very difficult to coat the whole surface uniformly with such biologically active material. Another problem involved in the coating of implants is found in that the adhesion of the coating to the base body is not sufficient to keep the coated implant effective for a long time under the severe conditions in the living body. In addition, the coating requires the use of a special expensive apparatus. Furthermore, the yield of the expensive hydroxyapatite is low and, therefore, no substantial coat-down is attainable.

In the art, besides the plasma-spray technique, there is also known a coating method in which a titanium base body of an implant is immersed in a solution containing Ca and P compounds and then the base body is baked so as to cover it with a layer of calcium phosphate. This method has an advantage that it does not impose so many limitations on the shape of the implant to be coated. However, an important drawback of the method is found in that the process of immersion coating—baking has to be repeated many cycles in order to form a film having a sufficient thickness for attaining the desired effect of the biological activity and that the process is complicated to carry out. In addition, the bio-active film obtained according to the method has an insufficient stability in the living body. In principle, by either of the above plasma-spray technique or the immersion—baking method, it is difficult to firmly coat the surface of a titanium base body with such ceramic material which is far different from the metal titanium. The two materials have a large difference in thermal expansion coefficient, crystal structure etc.

In the art there is also used the technique of anodic oxidation for attaining the above-mentioned purpose. In this method, a titanium anode and a cathode of, for example, stainless steel are placed in electrolyte solution and a voltage is applied between the two electrodes so that an oxidation film can be formed on the titanium anode as a result of the electrochemical oxidation of the titanium surface. Hitherto, this technique has been used, for example, for preparing colored titanium useful for accessories and architectural material. The colored titanium obtained according to this method is a kind of interference film the thickness of which is very small. The artificial dental root made of titanium can be colored in gold by employing the method. For this reason, this method has hitherto been used for color-matching of artificial dental root to gum. Compared with other known methods, this coating method has many advantages. Firstly, one can easily form a reactive oxidation film more than 1 μm thick. Secondly, the adhesion between the oxidation film and the base body is good. Thirdly, any base body having a complicated shape can be coated uniformly. Finally, it needs no special apparatus and only a short time is required for carrying out the treatment.

Though the anodic oxidation method has many advantages as mentioned above, it has been found that the affinity between an implant and bone tissue is not always improved by this method so long as the oxidation film is composed of titanium oxide only.

Under the circumstances, in order to obtain such implants which satisfy all of the desired characteristics, it is absolutely necessary for the anodic oxidation method to be further improved. The present invention has been made to overcome the disadvantages of the prior art methods as mentioned above.

SUMMARY OF THE INVENTION

An object of the present invention is to overcome the drawbacks involved in the prior art as mentioned above, and to provide an improved implant and a method of making the same.

More specifically, it is an object of the present invention to provide an implant comprising a core member having any desired shape and made of titanium or alloy thereof and a coating of biologically active material formed on the core member.

It is a further object of the invention to provide such implant coated with a biologically active material which is stable in the living body for a long time and excellent in the affinity to the bone tissue.

It is still a further object of the invention to provide a method of making such improved implant.

In order to attain the above objects, according to the present invention, there is provided an implant comprising a core member all or only the surface portion of which is made of titanium or alloy thereof and an anodic oxidation film formed on the core member, said oxidation film containing Ca and P. A method of making the implant is also provided according to the present invention.

Further, the present invention provides an implant and a method of making it which is characterized in that a calcium phosphate compound such as hydroxyapatite is precipitated on the above-described oxidation film.

The method of making the implant according to the present invention may comprise the steps of:

placing an implant having any desired shape and made of titanium or a titanium alloy in an electrolyte solution containing Ca-compound and P-compound;

subjecting the implant to an anodic oxidation so as to form an anodic oxidation film containing Ca and P on the surface of the impant; and optionally subjecting the formed film to a hydrothermal treatment thereby forming a film of calcium phosphate compound such as hydroxyapatite on the surface of the previously formed anodic oxidation film.

Other objects, features and advantages of the present invention will be apparent from the following description taken in connection with the accompanying drawings.

BRIEF DESCRIPTION OF THE DRAWINGS

FIG. 1 is a sectional view of a model of a dental implant;

FIG. 2 is a partly enlarged sectional view showing the area A of the dental implant shown in FIG. 1;

FIG. 3 is a sectional view of a model showing the state of the surface of a stem; and FIG. 4 is a partly enlarged sectional view showing the area B of the stem shown in FIG. 3.

DESCRIPTION OF THE PREFERRED EMBODIMENTS

Referring to FIG. 1, there is shown a model of a dental implant 1. As seen best in FIG. 2, the implant comprises a core 2, an anodic oxidation film 3 on the core and a film of calcium phosphate compound 4 precipitated on the anodic oxidation film 3. In FIG. 1, the implant is shown in the state implanted in an alveolar bone 5. Designated by 6 is a dental crown, 7 is superstructure and 8 is gum. In a further embodiment shown in FIGS. 3 and 4, the implant 13 comprises a core 9 with a number of titanium beads 10 sintered on it to form a porous structure, an anodic oxidation film 11 formed on the porous structure, and a film of calcium phosphate compound 12 precipitated on the anodic oxidation film 11. The present invention will be described in further details with reference to the above embodiments.

In the present invention, the core which constitutes the base body of an implant is composed of titanium or a titanium alloy and may have any desired shape. For example, the base body is in the form of a rod or plate which may have additionally pores therein or threads thereon. It may be also in the form of porous structure like a sponge or mesh structure as a woven material. The surface of the base body may be provided with a porous surface layer formed by plasma-spraying titanium powder or by sintering on the surface a number of titanium beads or titanium alloy beads.

Before being subjected to the anodic oxidation, the base body must be polished in the conventional manner and washed with alcohol or water. If the base body can not be polished, the surface of the base body should be cleaned well by pickling or the like. Those portions of the base body for which no anodic oxidation is necessary are previously covered with a masking agent. The masking agent may be removed after completing the treatment on the whole body. The surface of the base body may be subjected to a roughening treatment by etching or sand blasting. By doing so, the surface area of the base body can be enlarged to improve the adhesion of the surface to the film. This treatment has a further effect to remove any other film formed by spontaneous oxidation in the atmosphere and also to make the active surface of the base body exposed, thereby further improving the adhesion of the anodic oxidation film to the surface of the base body. After completing the above pretreatment, the base body is subjected to the anodic oxidation.

The electrolyte solution used for the anodic oxidation must contain at least a P-compound in order to obtain the necessary high electroconductivity. Simultaneously with the P-compound, a Ca-compound is also added to the electrolyte solution. By using such an electrolyte solution for the anodic oxidation, the formed anodic oxidation film can grow taking up Ca and P in it from the solution. As the result of it, there is formed an oxidation film on titanium anode which contains Ca and P. Examples of the Ca-compound suitably used in the invention include calcium chloride, calcium carbonate, calcium nitrate, calcium hydroxide, calcium acetate, calcium lactate, calcium glycerophosphate, calcium gluconate, calcium citrate and calcium propionate. These examples are not limitative. Among others, calcium acetate and calcium glycerophosphate are preferably used because they have a high solubility in water and contain no biologically toxic ion.

Examples of the P-compound suitably used in the invention include phosphoric acid, sodium α-glycerophosphate, sodium β-glycerophosphate, calcium glycerophosphate, 1-hydroxyethane-1,1-bis-phosphonate and phytic acid. Glycerophosphates are most preferred. They do not react with any of the above-mentioned calcium compounds when the latter is added to the solution simultaneously and therefore they do not produce any precipitate. Further, they allow the preparation of the electrolyte solution containing Ca and P in high concentrations and to permit the anodic oxidation to be carried out stably up to a high level of voltage.

The solvent for the electrolyte is not limited to water only. Other media such as organic solvent are also suitable. The titanium implant is immersed in the electrolyte solution and the anodic oxidation is carried out in the following manner.

The maximum electrolytic voltage for this anodic oxidation is preferably in the range of 10 V to 600 V. With a voltage lower than 10 V, the anodic oxidation is not possible. With a voltage higher than 600 V, the anodic oxidation is rendered unstable and some irregularity is produced in the anodic oxidation film. Since, as will be described later, the level of electrolytic voltage has a substantial effect on the composition of the film, and the surface structure of the film and/or the film thickness, the electrolytic voltage should be so selected as to optimize the above conditions. Electric current should be controlled in accordance with the surface area of the base body to be subjected to the anodic oxidation. With a large current, the electrolytic voltage rises rapidly and, therefore, the anodic oxidation may be completed in a shorter time. However, the use of a large current brings about the problems that the adhesion of the film is lowered and the uniformity of the micro-structure is disturbed. Therefore, it is preferable that the anodic oxidation should be carried out slowly, under a current as small as possible, so as to obtain higher adhesion of the film. The heat generated during the anodic oxidation brings about some decrease of the adhesion between the film and the base body. In order to avoid the adverse effect, the temperature of the electrolyte solution should be kept preferably at 0° C. or near 0° C. However, if the optional step of the hydrothermal treatment is carried out as described later, a higher temperature of the electrolyte solution, preferably, in the range of 5° C. to 60° C. should be used for the anodic oxidation. This is because, when the anodic oxidation film has been formed at the low temperature of 0° C. or near 0° C., the crystal of calcium phosphate such as hydroxyapatite may not readily precipitate on the formed film. The anodic oxidation may be carried out employing any known conventional method and apparatus.

The composition of the formed film can be determined depending on the composition of the electrolyte solution and the electrolytic voltage. Under the condition of a fixed voltage, the ratio of Ca to P contained in the oxidation film on the titanium anode is variable depending on the respective concentrations and the ratio of Ca- and P-compounds in the electrolyte solution. When the composition of the electrolyte solution is fixed, the ratio of Ca to P contained in the oxidation film on the titanium anode is variable depending on the electrolytic voltage.

Therefore, the ratio between the atoms which constitute the formed film, that is, Ca/Ti ratio, P/Ti ratio and Ca/P ratio may be controlled by suitably selecting the composition of the electrolyte solution as well as the electrolytic voltage. Thus, for example, one can obtain a film having high biological activity by letting the film take up P and Ca as much as possible while keeping the Ca/P ratio, for example, at the value of 1.67 which is the theoretical Ca/P ratio of the hydroxy-apatite. If desired, two or three electrolyte solutions having different compositions may be used to obtain a film whose composition is stepwise changed. To this end, during the anodic oxidation, the implant is anodic-oxidized in the different electrolyte solutions successively. It is also possible to obtain a film whose composition is continuously changed, by adding to the electrolyte solution, during the anodic oxidation, a solution having a higher content of Ca- and/or P-compounds.

After completing the anodic oxidation treatment, the treated surface of the implant can be cleaned by means of supersonic wave in distilled water. After cleaning, the implant can be used without any further treatment. However, if desired, the implant may be subjected additionally to a hydrothermal treatment in steam under elevated pressure before the use of the implant. The object of this treatment is to form a film of a calcium phosphate compound such as hydroxyapatite on the previously treated surface of the implant. The hydrothermal treatment is carried out preferably at a temperature in the range of 100° C. to 500° C. At a temperature lower than 100° C., the crystal of calcium phosphate cannot grow. At a temperature higher than 500° C., the adhesion between the formed film and the base body of the implant may be lowered and there may be brought about some other disadvantages. For this reason, the use of a temperature in the above specified range is preferred.

As described above, according to the invention, a biologically active film containing Ca and P is formed on the surface of an implant base body composed of titanium or titanium alloy by the technique of anodic oxidation on titanium anode. Since the film thus formed is a film of deposit from the implant surface constituted of titanium or titanium alloy, there exists a high crystal coherency between the film thus formed and the titanium or titanium alloy of the base body. Also, the adhesion strength of the film to the base body is high. For the same reason, the film of calcium phosphate compound such as hydroxyapatite additionally formed by precipitation on the oxidation film on anode previously formed has also a very high adhesion strength. Compared with the film formed by the conventional coating method in which a ceramic material that is completely different from metal is externally adhered to a metal base body, the film obtained according to the present invention has many advantages, namely, higher biomedical stability, longer useful life and higher resistance to separation of the film and to loss of the film by cellular resorption.

The oxidation film on titanium anode obtained according to the present invention contains Ca and P like a bone and the ions of Ca and P can leach from the film in the living body. Therefore, the film has an excellent affinity to bone tissue. In addition, in the living body, the film can spontaneously deposit a calcium phosphate such as hydroxyapatite on the surface of the implant. When the optional step of the hydrothermal treatment is employed, the precipitation of such calcium phosphate compound can be formed prior to the use of the implant. In either case, a direct bonding is obtained between the anodic oxidation film and the bone.

In the method of making the implant according to the present invention, the implant is immersed in the electrolyte solution and subjected to the anodic oxidation. Therefore, whatever shape the implant may have, all its surface in contact with the electrolyte solution may be uniformly coated except for a very small hole which the solution can not penetrate. Thus, the present invention is applicable even to implants having various complicated shapes and forms. The method according to the invention has many other advantages. It does not need any special apparatus. The time required for the anodic oxidation treatment is short, in the range of from several tens of seconds to several minutes. The operations necessary for carrying out the method are simple and easy to perform.

The following examples are given to illustrate the present invention in further detail.

EXAMPLE 1–3

As shown in the following Table 1, a base body of pure titanium was subjected to the anodic oxidation in an electrolyte solution containing P-compound and Ca-compound under the condition of 350 V.

As the P-compound, there was used phosphoric acid. As the Ca-compound there were used calcium acetate, calcium glycerophosphate and calcium citrate, respectively.

A film was obtained on the titanium base body. The color of the film was grayish black. The atom ratio of Ca/P contained in the film was under 1 with the content of P far larger than Ca.

EXAMPLES 4–6

As shown in Table 1, a base body of pure titanium was subjected to the anodic oxidation in an electrolyte solution containing P-compound and Ca-compound.

As the P-compound, there was used calcium glycerophosphate. The P-compound was dissolved in distilled water together with calcium acetate. In each of the examples 4–6, a grayish white film was obtained.

The concentration of calcium acetate was different in Examples 4 and 5. Under the condition of a fixed electrolytic voltage, the composition of the film to be formed was controlled by suitably changing the composition of the electrolyte solution. In Example 4, the ratio of Ca/P was set to 1.67 which is Ca/P ratio of hydroxyapatite. In Examples 5 and 6, the electrolyte solutions had the same composition. However, the voltage selected was 300 V for Example 5 and 350 V for Example 6. The compositions of the anodic oxidation films obtained in Examples 5 and 6 were different from each other. This means that the composition of the film can be determined depending on the electrolytic voltage.

EXAMPLES 7–11

As shown in Table 1, a base body of pure titanium was subjected to the anodic oxidation.

As the P-compound, there was used sodium β-glycerophosphate. The P-compound was dissolved in distilled water together with calcium acetate. Compared with the previous example in which calcium glycerophosphate was used, Ca/Ti ratio and P/Ti ratio in the present examples were increased, that is, the contents of Ca and P in the formed anodic oxidation film were increased and, as a result, the biological activity of the film was improved.

In Examples 7 and 8, the same electrolytic voltage of 330 V was used, but the concentrations of sodium β-glycerophosphate and calcium acetate were changed between the two examples. It was shown that the percentages of Ca and P contained in the formed film were also changed in response to the change of the concentrations of said compounds. The results demonstrate that the contents of P and Ca in the formed anodic oxidation film as well as the ratio of Ca/P were adjustable by changing the composition of the electrolyte solution. For example, we could easily adjust the ratio of Ca/P to 1.67 which is the theoretical value of Ca/P of hydroxyapatite.

In comparison between Examples 7 and 9 where only the electrolytic voltage was changed while using the electrolyte solutions having the same composition, it is seen that when the voltage was higher, the contents of Ca and P were higher.

Also, between Examples 8 and 10, there was a difference in applied voltage. However, compared with the case of Examples 7 and 9, the change in the content of Ca and P was less when the concentration of the electrolyte solution was low. It was observed in these examples that the anodic oxidation film grows taking up Ca and P from the solution and, therefore, the amount of P and Ca taken up per unit film thickness increases with increasing concentration of the solution, and that the contents of Ca and P in the film change to a larger extent when the concentration of the solution is higher.

In Example 11 where the concentration of the solution was relatively low, the anodic oxidation could be performed stably up to a very high voltage level. The film obtained in this example showed well-developed micro-projections which were expected to have a satisfactory micro-anchoring effect to the bone tissue.

The color of the films obtained in all of these examples was grayish white. The micro-structure of the films had the tendency to be irregular with the increase of the contents of Ca and P in the anodic oxidation film. With the increase of the concentration of the solution, the attainable level of electrolytic voltage was rendered lower. When the concentration approached the supersaturation, the solution clouded. For these reasons, it is preferred that the anodic oxidation should be carried out at an optimum concentration of the solution.

The adhesion strength of the films obtained in these examples was measured to be in the range of 30 to 35 MPa which is sufficient for implants in practice.

EXAMPLES 12–13

As shown in Table 1, a base body of pure titanium was subjected to the anodic oxidation in an aqueous solution of sodium β-glycerophosphate. The film obtained at the concentration of 0.07 mol/l was colored grayish black. However, when calcium acetate was added to the solution, the film was turned to grayish white. A grayish white film was obtained also when the concentration of the aqueous solution of sodium β-glycerophosphate was increased up to 0.13 mol/l. Thus, it was possible to obtain an oxidation film on titanium anode in grayish white even when sodium β-glycerophosphate was used alone.

EXAMPLES 14–15

A base body of Ti6A14V alloy was subjected to the anodic oxidation. A light brown film was obtained. Like the previous examples in which titanium base body was used, the anodic oxidation film containing Ca and P was formed in the present examples. In addition to Ca and P, the formed film contained a trace of the oxides of Al and V. The present examples also demonstrate that the contents of Ca and P are variable depending on the concentration of the solution.

TABLE 1

| Example No. | Base body | Composition of electrolyte solution | | | | Electrolytic potential | Atom ratio of film | | | Color of film |
|---|---|---|---|---|---|---|---|---|---|---|
| | | P compound | Concentration | Ca compound | Concentration | | Ca/Ti | P/Ti | Ca/P | |
| 1 | Ti | phosphoric acid | 0.26M | calcium acetate | 0.10M | 350 V | 0.31 | 1.98 | 0.21 | grayish black |
| 2 | " | phosphoric acid | " | calcium glycerophosphate | 0.14 | " | 0.34 | 1.42 | 0.24 | grayish black |
| 3 | " | phosphoric acid | " | calcium citrate | 0.04 | " | 0.41 | 1.52 | 0.27 | grayish black |
| 4 | " | calcium glycerophosphate | 0.07 | calcium acetate | 0.37 | 300 | 0.37 | 0.22 | 1.67 | grayish white |
| 5 | " | calcium glycerophosphate | 0.07 | calcium acetate | 0.29 | " | 0.38 | 0.26 | 1.42 | grayish white |
| 6 | " | calcium glycerophosphate | 0.07 | calcium acetate | 0.29 | 350 | 0.47 | 0.28 | 1.67 | grayish white |
| 7 | " | sodium β-glycerophosphate | 0.12 | calcium acetate | 0.50 | 330 | 1.04 | 0.64 | 1.63 | grayish white |
| 8 | " | sodium β-glycerophosphate | 0.06 | calcium acetate | 0.30 | 330 | 0.50 | 0.31 | 1.64 | grayish white |
| 9 | " | sodium β-glycerophoshate | 0.12 | calcium acetate | 0.50 | 300 | 0.68 | 0.41 | 1.67 | grayish white |
| 10 | Ti | sodium β-glycerophosphate | 0.06 | calcium acetate | 0.30 | 360 | 0.57 | 0.31 | 1.85 | grayish white |
| 11 | " | sodium β-glycerol phosphate | 0.04 | calcium acetate | 0.20 | 390 | 0.57 | 0.34 | 1.71 | grayish white |
| 12 | " | sodium β-glycerophosphate | 0.07 | — | — | 300 | 0 | 0.38 | 0 | grayish black |
| 13 | " | sodium β-glycerophosphate | 0.13 | — | — | " | 0 | 0.44 | 0 | grayish white |
| 14 | Ti6Al4V | sodium β-glycerophosphate | 0.16 | calcium acetate | 0.40 | " | 1.51 | 1.12 | 1.36 | light brown |
| 15 | " | sodium β-glycerophosphate | 0.12 | calcium acetate | 0.50 | " | 0.83 | 0.54 | 1.54 | light brown |

The anodic oxidation films obtained in Examples 4 to 11 and Examples 14 and 15 were examined by a scanning electron microscope to observe their micro-structures. It was found that there was no substantial difference in microstructure between titanium and alloy of titanium, that the formation of pores and microprojections was initiated with spark discharge and that larger pores and microprojections could be formed under higher electrolytic voltage.

EXAMPLE 16

The anodic oxidation films obtained in Examples 4 to 11 and Examples 14 and 15 where glycerophosphate and calcium acetate were simultaneously used for the anodic oxidation were introduced into an autoclave and subjected to hydrothermal treatment for two hours at 300° C. in high pressure steam. After the treatment, each film was examined as to whether any film of calcium phosphate compound was formed additionally on the previously formed anodic oxidation film. For every film, an analysis by X-ray diffraction and a Fourier transform infrared spectroscope showed the formation of a hydroxyapatite film.

The anodic oxidation films formed in Examples 6–11 were observed, after the hydrothermal treatment, through a scanning electron microscope with regard to the film surface. It was found that a large amount of hydroxyapatite crystals were precipitated on the anodic oxidation film which naturally contained Ca and P so that the whole surface of the anodic oxidation film was covered with a 1 to 3 μm thick film of hydroxyapatite. The observation also showed that the hydroxyapatite crystals begin to precipitated on the film surface compactly, leaving no space between the crystals when the content of Ca and P in the anodic oxidation film have exceeded a certain level.

The hydrothermal treatment was applied also to the implant having a porous structure formed by sintering a number of titanium beads on the core body. Having been subjected to the anodic oxidation, the implant with titanium beads was subjected additionally to the hydrothermal treatment as described above. After completing the hydrothermal treatment, the surface of the implant was carefully examined. All the surface was found to be covered with hydroxyapatite crystals. Not only the surface of the uppermost layer of beads, but also the surfaces of beads in deeper layers in direct contact with the surface of the core body were completely covered, including the bottom surfaces of the beads.

EXAMPLE 17

Pure titanium was anodized in an electrolyte containing sodium β-glycerophosphate (molecular weight 306) and calcium acetate (molecular weight 176), under the conditions of the electrolytic voltage of 350 V, current density of 50 mA/cm$^2$ and electrolyte temperature of 0° to 50° C. followed by a hydrothermal treatment conducted for two hours in a high-pressure steam of 300° C. Then, the mean attached strength of the film and the state of precipitation of hydroxyapatite were examined to obtain results shown in Table 2.

histology as in other cases.

The values of the Ca/P ratio of the hydroxyapatite crystals, obtained through hydrothermal treatment of anodic oxide films formed at various concentration levels, shown in Table 2, substantially conformed with the stoichiometric compositional ratio (1.67). It was also confirmed that the Ca/P ratio of the precipitated hydroxyapatite crystals at each level of sodium β-glycerophosphate can be finely adjusted by slightly changing each value of the calcium acetate concentration shown in Table 2. It was thus easy to produce Ca-deficient hydroxyapatite crystals which are said to have high compatibility to bone.

The hydroxyapatite crystals thus obtained were single crystals or crystals of very high crystallinity so that they advantageously exhibit small tendency of degradation in the living body.

TABLE 2

| Electrolyte concentration (mol/l) | | Film attached strength (Mpa) | | | | | | State of precipitation | Ca/p ratio of | |
|---|---|---|---|---|---|---|---|---|---|---|
| sodium β-glycero- | calcium | Electrolyte temp - (°C.) | | | | | | of hydroxy-apatite | hydroxy-apatite | Film |
| phosphate | acetate | 0 | 10 | 20 | 30 | 40 | 50 | crystals | crystals | color |
| 0.01 | 0.15 | 38 | 38 | 38 | 39 | 39 | 41 | Covered substantially entire area | 1.67 | white |
| 0.02 | 0.20 | 40 | 30 | 26 | 22 | 19 | 19 | covered entire area | 1.66 | white |
| 0.03 | 0.25 | 22 | 18 | 14 | 13 | 11 | 13 | covered entire area | 1.68 | grayish white |
| 0.04 | 0.25 | 20 | 17 | 14 | 13 | 13 | 13 | covered entire area | 1.65 | grayish white |
| 0.05 | 0.25 | 17 | 18 | 20 | 24 | 21 | 17 | covered entire area | 1.67 | grayish white |
| 0.06 | 0.30 | 14 | 16 | 17 | 21 | 17 | 12 | covered entire area | 1.68 | grayish white |

As will be clear from Table 2, a tendency was observed that the lower the concentration of the electrolyte, the higher the film attached strength. More specifically, the attached strength was high and was not lowered in relation to time in the living body, particularly when the concentration of sodium β-glycerophosphate was 0.01 mol/l or when this concentration was 0.02 mol/l while the electrolyte temperature was low. A tendency was also observed that the lower the electrolyte concentration the lower the amount of precipitation of the hydroxyapatite crystals. However, it is to be noted that even when the concentration of sodium β-glycerophosphate was as low as 0.01 mol/l, compatibility to bone was considered to be excellent from the view point of

EXAMPLE 18

A porous layer having two layers of titanium beads of a mean particle size of 0.6 mm, formed on a titanium substrate (core) by sintering, was anodized in an electrolyte containing sodium β-glycerophosphate (molecular weight 306) and calcium acetate (molecular weight 176), under the conditions of the electrolytic voltage of 230 V, current density of 50 mA/cm$^2$ and electrolyte temperature of 30° C., followed by a hydrothermal treatment conducted for 2 hours in a high-pressure steam of 300° C. Then, the state of precipitation of hydroxyapatite was examined through an electron microscope to obtain the results shown in Table 3.

TABLE 3

| Electrolyte concentration (mol/l) | | State of precipitation of hydroxyapatite crystals | Ca/p ratio of hydroxyapatite crystals | Film color |
| --- | --- | --- | --- | --- |
| sodium β-glycero-phosphate | calcium acetate | | | |
| 0.04 | 0.30 | covered substantially entire area | 1.64 | grayish white |
| 0.06 | 0.40 | covered entire area | 1.65 | " |
| 0.08 | 0.50 | " | 1.67 | " |
| 0.10 | 0.55 | " | 1.66 | " |
| 0.12 | 0.60 | " | 1.67 | " |

As will be clear from Table 3, a tendency was observed that the higher the concentration of the electrolyte, the higher the amount of precipitation of hydroxyapatite crystals. More specifically, hydroxyapatite crystals were precipitated on the surfaces of all the beads and the bottom surface without any gap, when the concentration of sodium β-glycerophosphate was 0.06 mol/l or higher. The values of the Ca/P ratio of the hydroxyapatite crystals, obtained under the described conditions, substantially conformed with the stoichiometric compositional ratio. The hydroxyapatite crystals thus obtained were single crystals or crystals of very high crystallinity.

FIGS. 3 and 4 are schematic illustrations of the described implant after elapse of three months from implantation in bone tissues.

An anodized layer 11 and a hydroxyapatite layer 12 are formed on the surfaces of beads 10 sintered on the surface of the titanium core 9 of the implant 13, as well as on the bottom surface, so that newly formed bone well filled even small gaps between the beads 10, thus offering improved compatibility to the bone tissue 5 as compared with the untreated titanium bead porous body.

The described conditions are preferably adopted particularly when the voltage can hardly be raised due to too small pore size as are the cases of a porous layer obtained by sintering the titanium beads or porous titanium having micropores, although the invention is not limited to these porous structures.

The implants obtained according to the present invention have the following advantages over implants of the prior art.

The implant according to the present invention has micro-projections formed on the surface and/or micro-pores as formed by spark discharge. When the implant has been implanted in a bone and enveloped in bone tissue, a micro-anchoring effect is given by the micro-projections. Further, bone, some ingredients of bone such as collagen and other biological components may penetrate into the micro-pores, which will enhance a mechanical force for the retention of the implant. These mechanical engagements between implant and bone tissue all together bring forth a substantial improvement on the retention of the implant.

The anodic oxidation film formed on the implant has an effect to markedly reduce the elution of biologically toxic metal ions.

As shown in Examples 4–11 and 13, the method according to the present invention enables preparation of implants colored in grayish white. Compared with the metalic color of the untreated titanium implant, the grayish white may give a better impression to many patients because of its preferable appearance of cleanliness.

In the present method, the temperature at which the implant is treated is at or near 0° C., and, therefore, any substance useful for promoting the mineralization of bone and any biologically active substance cannot be deactivated by the treatment and rather can advantageously be conjugated. An example of the mineralization promoting substance is protein such as so-called bone morphogenetic protein. An example of the biologically active substance is sodium β-glycerophosphate.

The film of hydroxyapatite optionally formed by the hydrothermal treatment has also such an advantage that it can be formed at a very low temperature compared with the prior art method such as sintering and plasma-spray coating. As a result, there is obtained such hydroxyapatite which is very similar, in terms of crystallization, to the hydroxyapatite constituting bones. This means that the implant exhibits very good affinity to bones.

Apart from the application as biomaterial, the anodic oxidation film covered with a layer of such hydroxyapatite can be used also as adsorbent for chromatography. The oxidation film on titanium anode and containing Ca and P as obtained according to the present invention is porous and has a large specific surface area. Therefore, the film may be used not only for implant but also for catalyst, electronic material, adsorbent etc. and a further improvement of their functions may be attained.

What is claimed is:

1. An implant comprising:

an implant base body, at least a surface portion of which is composed of one of titanium and titanium alloy; and an anodic oxidation film formed on said surface portion of the implant base body, said film containing mainly ionic Ca and P.

2. An implant according to claim 1, wherein a calcium phosphate compound is precipitated on said anodic oxidation film.

3. A method of making an implant, comprising:

subjecting an implant base body, at least a surface portion of which is composed of one of titanium and titanium alloy, to anodic oxidation in an electrolytic solution containing Ca ion and P ion or phosphoric ion to form an anodic oxidation film on the body; and subjecting the anodic oxidized body to a hydrothermal treatment in a high pressure steam, thereby precipitating a calcium phosphate compound on the anodic oxidation film.

4. An implant prepared according to the method of claim 3.

5. An electrolyte for the preparation of an implant comprising, as main components, glycerophosphate and a salt of calcium.

6. A method of making an implant, comprising:
subjecting an implant base body, at least a surface portion of which is composed of one of titanium and titanium alloy, to anodic oxidation in an electrolytic solution containing glycerophosphate and calcium salt as main electrolyte ingredients.

7. An implant prepared according to the method of claim 6.

* * * * *